United States Patent
Knapp et al.

(10) Patent No.: US 12,426,854 B2
(45) Date of Patent: Sep. 30, 2025

(54) COORDINATING SCANNERS IN AN ULTRASOUND CART

(71) Applicant: FUJIFILM SONOSITE, INC., Bothell, WA (US)

(72) Inventors: David Knapp, Bellevue, WA (US); Kenji Kimura, Seattle, WA (US); Tyler Dawson, Edmonds, WA (US); Craig Chamberlain, Seattle, WA (US); Andrew Lundberg, Seattle, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 141 days.

(21) Appl. No.: 17/982,865

(22) Filed: Nov. 8, 2022

(65) Prior Publication Data

US 2024/0148362 A1    May 9, 2024

(51) Int. Cl.
*A61B 8/00* (2006.01)
*A61B 90/00* (2016.01)

(52) U.S. Cl.
CPC .......... *A61B 8/4472* (2013.01); *A61B 8/4405* (2013.01); *A61B 8/4422* (2013.01); *A61B 8/4433* (2013.01); *A61B 8/4477* (2013.01); *A61B 8/462* (2013.01); *A61B 8/465* (2013.01); *A61B 8/469* (2013.01); *A61B 8/54* (2013.01); *A61B 8/56* (2013.01); *A61B 8/486* (2013.01); *A61B 8/488* (2013.01); *A61B 90/08* (2016.02)

(58) Field of Classification Search
None
See application file for complete search history.

(56) References Cited

U.S. PATENT DOCUMENTS

| | | | |
|---|---|---|---|
| 2018/0263600 A1* | 9/2018 | Bell | A61B 8/4472 |
| 2019/0059855 A1* | 2/2019 | Jin | A61B 8/4472 |
| 2019/0343483 A1* | 11/2019 | Kanakasabhapathi | G01S 7/52079 |
| 2019/0365352 A1* | 12/2019 | Song | A61B 8/56 |
| 2019/0383920 A1* | 12/2019 | Kook | G01S 7/52053 |

(Continued)

OTHER PUBLICATIONS

Sonohealth (https://www.youtube.com/watch?v=IRIADUxODhw, (Sep. 29, 2020), retrieved on Aug. 20, 2024) (Year: 2020).*

*Primary Examiner* — Keith M Raymond
*Assistant Examiner* — Ashish S Jasani
(74) *Attorney, Agent, or Firm* — Womble Bond Dickinson (US) LLP

(57) ABSTRACT

This disclosure provides systems, devices, methods, and apparatus, for coordinating scanners in an ultrasound cart. An ultrasound system can include an ultrasound cart having a scanner holder configured to hold ultrasound scanners, a display device configured to display a visual representation of the scanner holder, and at least one of the ultrasound scanners. The visual representation can be implemented to identify locations of the ultrasound scanners on the scanner holder. The ultrasound scanners can be configured to indicate, while being held in the scanner holder, that one ultrasound scanner of the ultrasound scanners is to be selected for an ultrasound examination. The ultrasound scanner can also be configured to implement a first ultrasound imaging mode when a display device is attached to the ultrasound cart, and a second ultrasound imaging mode and not the first ultrasound imaging mode when the display device is removed from the ultrasound cart.

9 Claims, 11 Drawing Sheets

(56) References Cited

U.S. PATENT DOCUMENTS

2020/0008785 A1* 1/2020 Lee .................... A61B 8/00
2022/0202522 A1* 6/2022 Czupi .................. G08B 5/36
2024/0315666 A1* 9/2024 Rousseau ............ A61B 8/4477

* cited by examiner

COORDINATING SCANNERS IN AN ULTRASOUND CART

TECHNICAL FIELD

The present disclosure relates generally to ultrasound systems, and more particularly, to coordinating scanners in an ultrasound cart.

BACKGROUND

Wired scanners can complicate many aspects of point of care ultrasound (POCUS) systems. For example, wired scanners can complicate transportation where cords interfere with casters, complicate cleaning due to cords dragging on the ground and adding more surface area to clean, and/or complicate finding the active scanner through tangled cords. Wired scanners can also limit a freedom of movement of clinical users around the ultrasound system and hinder image acquisition with tension in the cable that pulls on the scanner. Accordingly, wires of the wired scanners tend to be a point of failure that cause departments to incur expensive replacement costs and can defer patient treatment.

BRIEF SUMMARY

The following presents a simplified summary of one or more aspects in order to provide a basic understanding of such aspects. This summary is not an extensive overview of all contemplated aspects. This summary neither identifies key or critical elements of all aspects nor delineates the scope of any or all aspects. Its sole purpose is to present some concepts of one or more aspects in a simplified form as a prelude to the more detailed description that is presented later.

In an aspect of the disclosure, a system, method, and apparatus are provided. For example, the system can be an ultrasound system including an ultrasound cart having a scanner holder configured to hold ultrasound scanners. The system can also include a display device configured to display a visual representation of the scanner holder, the visual representation implemented to identify locations of the ultrasound scanners on the scanner holder. The system can also include at least one of the ultrasound scanners.

In another aspect of the disclosure, a system, method, and apparatus are provided. For example, the system can be an ultrasound system including an ultrasound cart having a scanner holder configured to hold ultrasound scanners. The system can also include the ultrasound scanners configured to indicate, while being held in the scanner holder, that one ultrasound scanner of the ultrasound scanners is to be selected for an ultrasound examination.

In another aspect of the disclosure, a system, method, and apparatus are provided. For example, the system can be an ultrasound system including an ultrasound cart including a processor. The system can also include an ultrasound scanner wirelessly coupled to a display device, and the display device implemented to be removably attached to the ultrasound cart. The processor, the display device, and the ultrasound scanner can be configured to implement a first ultrasound imaging mode when the display device is attached to the ultrasound cart. The display device and the ultrasound scanner can be configured to implement a second ultrasound imaging mode and not the first ultrasound imaging mode when the display device is removed from the ultrasound cart.

To the accomplishment of the foregoing and related ends, the one or more aspects correspond to the features hereinafter described and particularly pointed out in the claims. The one or more aspects can be implemented through any of an apparatus, a method, a means for performing the method, and/or a system. The following description and the drawings set forth in detail certain illustrative features of the one or more aspects. These features are indicative, however, of but a few of the various ways in which the principles of various aspects can be employed.

BRIEF DESCRIPTION OF THE DRAWINGS

The appended drawings illustrate examples and are, therefore, exemplary embodiments and not considered to be limiting in scope.

DETAILED DESCRIPTION

The portability of wireless scanners may be of reduced benefit in some cases as a result of battery reductions that occur over time and/or that multiple scanners can have to acquire different views. However, wireless scanners can provide an advancement in cart-based systems as well, e.g., by resolving many of the issues/drawbacks associated with wired scanner systems. Further, a short battery life might be mitigated by keeping the battery charged and located on the cart system. Ultrasound exams are generally of short duration (e.g., 5-15 minutes), which can be suitable for a current wireless battery charge when the battery is able to be recharged immediately afterwards. However, in order to integrate wireless scanners into cart-based POCUS systems, users may have to determine how to store several wireless devices on the cart, how to charge the scanners, how to pair the scanners, and/or how to integrate paired scanners into the user interface.

Figure 1:
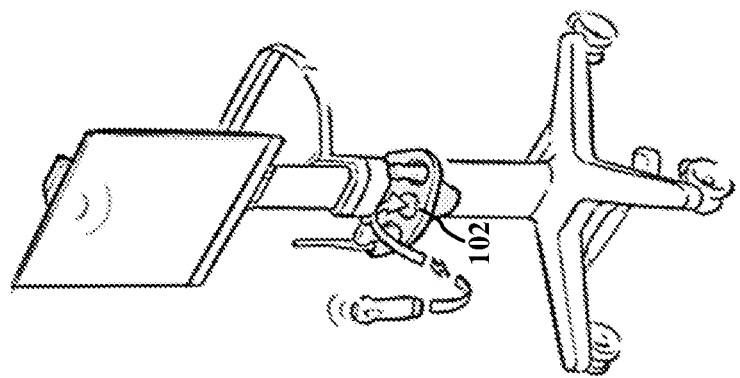
FIG. 1 illustrates a diagram of a smart scanner holder.

FIG. 1 illustrates a diagram 100 of a smart scanner holder 102 for wired and/or wireless scanners. In examples, wireless scanners (e.g., ultrasound scanners) can be integrated into storage, charging, and pairing in point of care ultrasound (POCUS) cart-based systems. Wireless scanners can be configured as portable devices, which can connect to phones, tablets, etc.

A POCUS cart-based system can include smart scanner holders 102 for managing multiple scanners on the system.

The scanner holders 102 can be configured to charge the scanners, either by wired connection or wirelessly based on an implementation, such as inductive charging. The scanner holders 102 can also automatically pair an unpaired scanner to the system when the unpaired scanner is within a communication range of the system. Light-emitting diodes (LEDs) can be used to indicate a state of each scanner to the user, including charging and active states, as some protocols may direct users to use different scanners within a workflow.

The scanner holders 102 can also indicate the specific scanner location for the system to display the order of the scanners. Having the physical location of the scanners represented in the digital user interface can help orient users to the various scanners. The scanner holders 102 can also allow the cart-based system to preprocess data transmitted through the wireless scanners.

Figure 2:
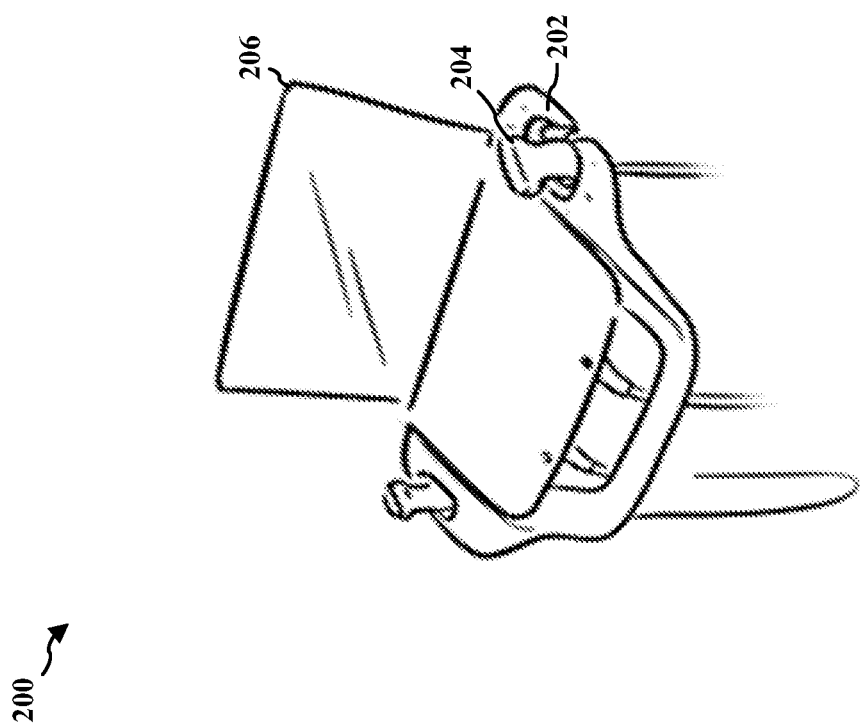
FIG. 2 illustrates a diagram of an example scanner holder on an ultrasound cart.

FIG. 2 illustrates a diagram 200 of an example scanner holder 202 on an ultrasound cart. The scanner holder 202 and a scanner 204 can be in communication with each other. For example, the communication can be through a low power communication link, such as Bluetooth®. The scanner 204 may be selected by a user or automatically by the ultrasound system. When the scanner 204 is selected, the scanner holder 202 and/or the ultrasound scanner 204 can indicate the selection, such as by emitting light via a light source (e.g., one or more LEDs).

A display device 206 can be used to indicate the scanner holder 202 and scanners 204. The display device 206 can include a tablet, smart-phone, ultrasound machine, smart glasses, smart contact lenses, etc., that can be implemented to display information related to an ultrasound examination, such as a user interface, ultrasound image, and the like. In some examples, the ultrasound system includes one or more ultrasound scanners 204, an ultrasound cart, and the display device 206. The ultrasound cart includes a scanner holder 202 configured to hold the ultrasound scanners 204. In one example, the display device 206 can be removably attached to the ultrasound cart, and can display information regarding the ultrasound scanners 204 and the scanner holder 202. For example, the display device 206 can display a visual representation of the scanner holder 202 and the locations of the scanners 204 in the scanner holder 202. The visual representation can include an icon in the shape of the scanner holder 202, and indicate an order of the ultrasound scanners 204 for use in an ultrasound examination, such as according to a protocol, e.g., extended focused assessment with sonography in trauma (E-FAST).

Figure 3:
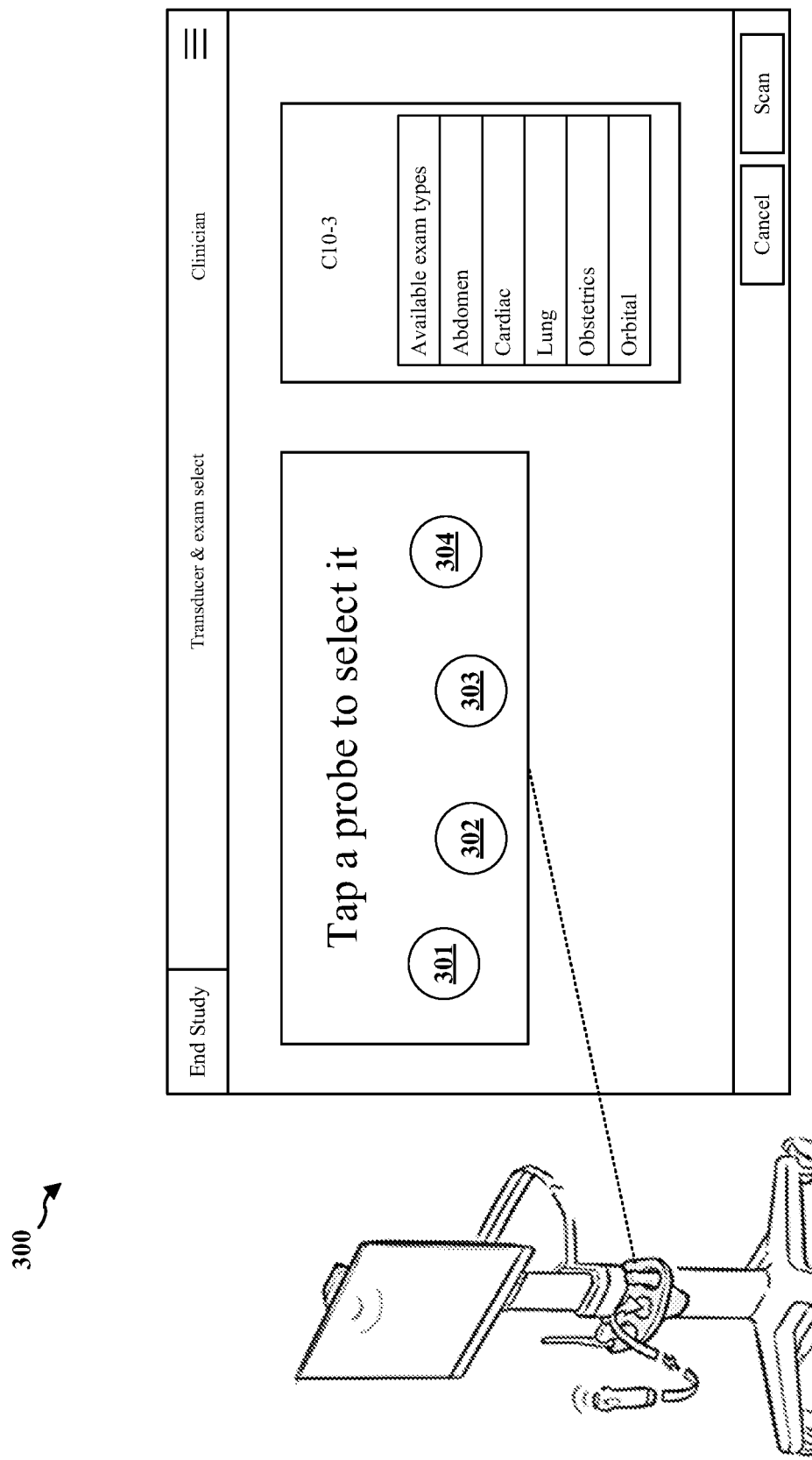
FIG. 3 is a diagram that illustrates a user interface of a display device with a visual representation of a scanner holder.

FIG. 3 is a diagram 300 that illustrates a user interface of a display device with a visual representation of a scanner holder. For example, the diagram 300 can be an example of information displayed on the display device 206 in FIG. 2. In the diagram 300, four ultrasound scanners are indicated by the circles 301, 302, 303, and 304 of the visual representation. The visual representation can indicate an order of ultrasound scanners, including a next ultrasound scanner to be selected for the ultrasound examination, in any suitable way, such as with colors, numbers, flashing/blinking icons, arrows, opacity changes, etc. The circles 301, 302, 303, and 304 can be arranged in a same shape as the scanner holder. For instance, the circles 301-304 can represent the physical locations of the scanner positions in the scanner holder. In the example in FIG. 3, the circles 301-304 are not co-linear, because the scanner locations in the scanner holder are not co-linear.

In the example illustrated by diagram 300, a user can tap an icon of a scanner location (e.g., a circle 301-304), to select a scanner. In response to the user selection, the ultrasound system can pair the selected scanner with the display device and/or the ultrasound cart, and the display device can remain on the ultrasound cart or be removed from the ultrasound cart to perform the ultrasound examination. The visual representation can indicate that at least one of the ultrasound scanners is paired with the display device, such as with an added icon (e.g., a pairing icon) or by modifying an existing icon (e.g., making one of the circles 301-304 corresponding to the paired scanner blink or flash).

The scanner and display device can pair using any suitable technology, such as near field communications (NFC), an optically read icon, etc. The pairing can be done automatically in response to the user selection in the user interface, e.g., using a NFC wireless protocol, such as Bluetooth®. Additionally or alternatively, the ultrasound scanner can include a display interface, label, sticker, etc., that displays a pattern, such as a quick response (QR) code, bar code, animation sequence, and the like, and the display device can include a reader configured to read the pattern on the scanner and facilitate the pairing based on the read pattern.

In one example, the ultrasound scanner and the display device are implemented to pair with each other responsive to the ultrasound scanner being removed from the scanner holder. Additionally or alternatively, the display device and the ultrasound scanner can terminate the pairing with each other responsive to the ultrasound scanner being returned to the scanner holder.

Figure 4:
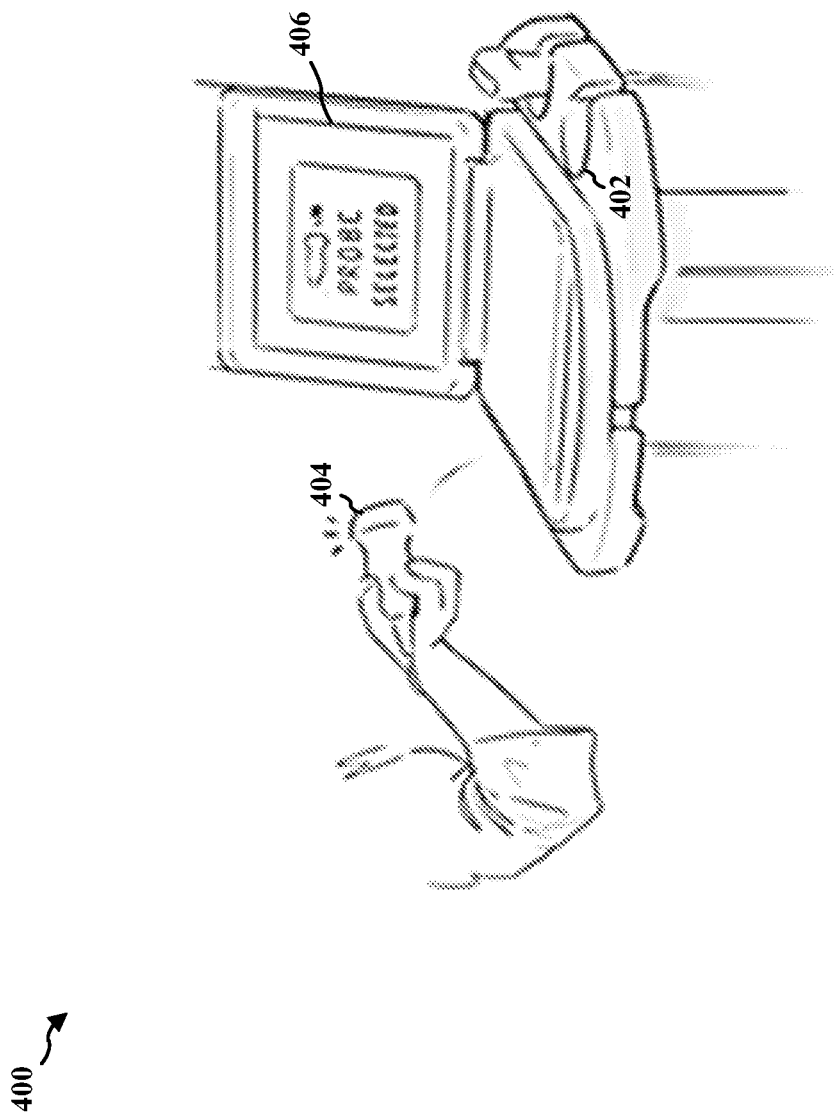
FIG. 4 is a diagram that illustrates pairing a scanner with a display device based on a gesture.

FIG. 4 is a diagram 400 that illustrates pairing a scanner 404 with a display device 406 based on a gesture. In an example, the scanner 404 includes an inertial measurement unit (IMU) configured to generate orientation data, such as six degrees of freedom data, yaw, pitch, and roll angles, etc. The user can perform a gesture with the scanner 404, such as by tracing an "X" or question mark in the air, and based on the gesture, the scanner 404 can pair with the display device 406. Additionally or alternatively, a camera, such as a camera in the display device 406 or the ultrasound cart, can detect the gesture and initiate the pairing. Additionally or alternatively, the ultrasound cart can determine that a user has removed a scanner 404 from the scanner holder 402, and in response, initiate the pairing. Additionally or alternatively, other gestures can be used such as moving the scanner 404 in a particular manner (e.g., shaking the scanner 404, rotating the scanner 404, waving the scanner 404, etc.). Alternatively or additionally, the gesture that is performed can make the scanner 404 active (as opposed to or in addition to pairing). Note that the results of removing the scanner 404 from the scanner hold 402 can cause the system to provide feedback and/or an indication to the user. For example, such feedback from the system can indicate that the user has selected the correct scanner 404 for the upcoming examination.

In one example, the scanner holder 402 includes a battery charger to charge a battery of the ultrasound scanners 404. For example, the ultrasound scanners 404 can be wireless and include a rechargeable battery that can be charged when the scanners 404 are placed in the scanner holder 402. Additionally or alternatively, the ultrasound cart can include a battery charger to charge a battery of the display device 406. The battery chargers of the ultrasound cart can use any suitable type of charging, such as inductive charging, charging over one or more connectors, etc.

In an example, the ultrasound cart includes a wireless hub configured to simultaneously communicate wirelessly with at least one of the ultrasound scanners 404 and/or an access point in a care facility. Hence, the scanner 404 can be used for an ultrasound examination, and during the ultrasound examination, the scanner 404 can communicate ultrasound data to the ultrasound cart, which can communicate the ultrasound data, during the examination, to a server (e.g., an archiver) of the care facility, such as for inclusion in a patient record. The wireless hub can operate according to one or more Wi-Fi protocols, and can include multiple transceivers to accomplish simultaneous communications over different communication links.

Figure 5:
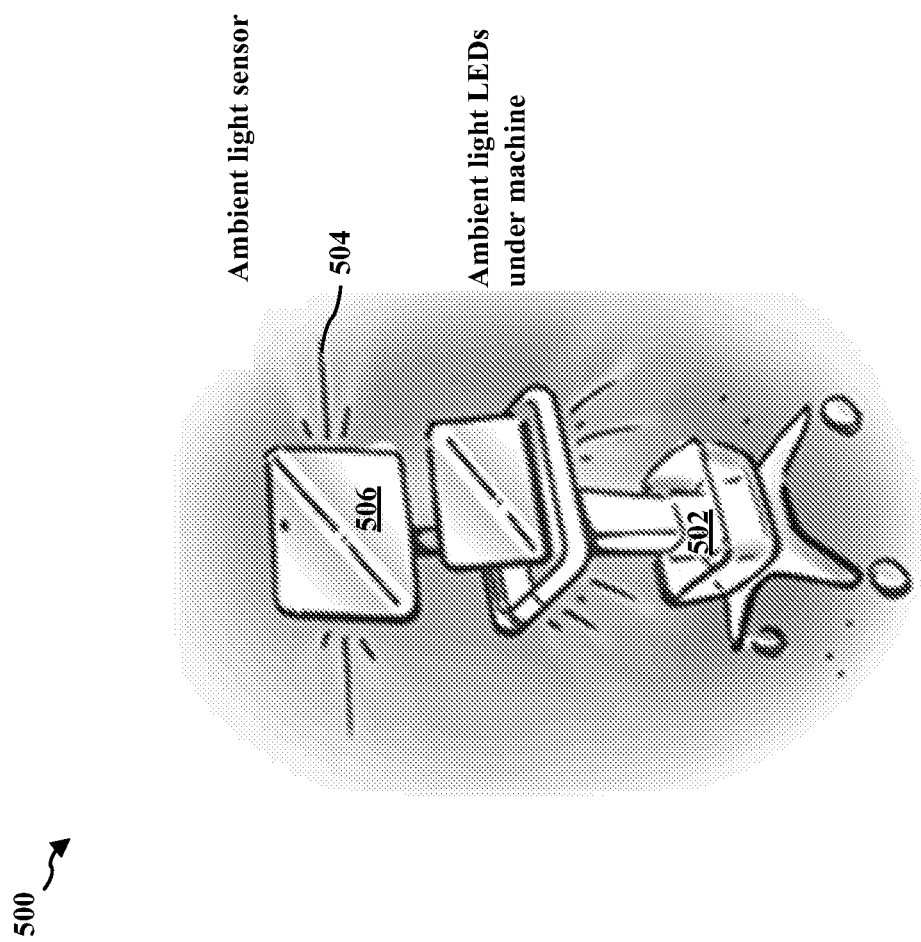
FIG. 5 is a diagram that illustrates backlighting a display screen and/or an ultrasound machine.

FIG. 5 is a diagram 500 that illustrates backlighting a display screen of a display device 506 and/or the ultrasound machine 502. In an example, the display device 506 is implemented to be attached to the ultrasound cart 502, and the ultrasound cart 502 includes a light source 504 configured to emit light such that a display screen of the display device 506 is backlit. By backlighting the display screen, the visual contrast ratio is improved compared to not backlighting the display screen, which is advantageous for the clinician, and hence also for the patient.

Clinicians often turn down the lighting in the room so that they can better see the display screen. Hence, the ultrasound cart 502 can include a light sensor that detects the amount of light in the room. If the light sensor detects that the amount of light in the room is below a threshold, and a scanner is paired with the display device 506 mounted to the ultrasound cart 502 for use, then the ultrasound cart 502 can automatically backlight the display screen.

Figure 6:
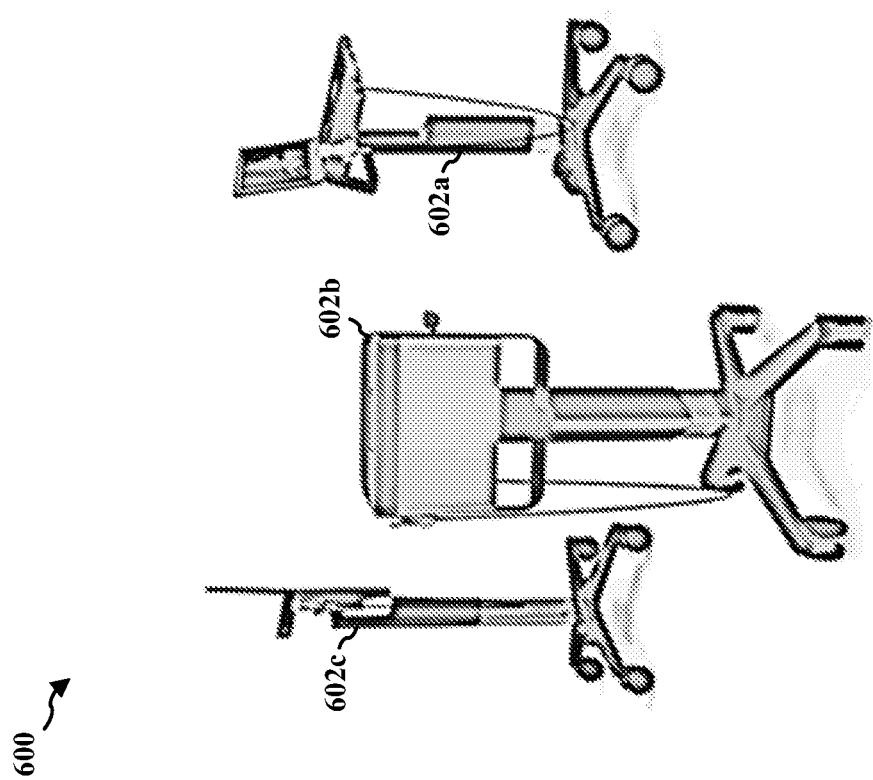
FIG. 6 is a diagram that illustrates a scanner holder that holds the scanners level in different cart orientations.

FIG. 6 is a diagram 600 that illustrates a scanner holder that holds the scanners level in different cart orientations 602a, 602b, 602c. In some embodiments, the ultrasound cart can be configured in multiple physical orientations 602a, 602b, 602c, such as in a first orientation 602a in which the ultrasound system is ready for use, and a second orientation 602b in which the ultrasound system is not ready for use, e.g., it is being moved from one location to another location. The scanner holder can be implemented to hold the ultrasound scanners in a level position when the ultrasound cart is configured in the multiple physical orientations 602a, 602b, 602c and as it transitions between the configurations. In some embodiments, the level position can be maintained by having the holder coupled to the cart using a coupling that independently swivels.

Additionally or alternatively to the display screen displaying a visual representation of the scanner holder and/or scanners, the scanners held by the scanner holder can communicate information to the user. In an example, an ultrasound system includes an ultrasound cart having a scanner holder configured to hold ultrasound scanners, and the ultrasound scanners that are configured to indicate, while being held in the scanner holder, that one ultrasound scanner of the ultrasound scanners is to be selected for an ultrasound examination. For instance, the one ultrasound scanner can be the next suitable ultrasound scanner for a protocol, like EFAST, being performed.

The one ultrasound scanner can include at least one light source configured to emit light to indicate that the one ultrasound scanner is to be selected for the ultrasound examination. For instance, the light source can include one or more LEDs (e.g., a matrix of LEDs) that are implemented to display a pattern to indicate that the one ultrasound scanner is to be selected for the ultrasound examination. Additionally or alternatively, the light source can change the color of the light to indicate that the one ultrasound scanner is to be selected for the ultrasound examination.

In one example, the ultrasound scanners include light sources configured to emit light to indicate an order that the ultrasound scanners are to be selected for the ultrasound examination. For example, the number of LEDs that are lit can indicate the order, such as one LED to indicate a first scanner to be selected, two LEDs to indicate a second scanner to be selected, three LEDs to indicate a third scanner to be selected, etc. Additionally or alternatively, the LEDs can be arranged in a matrix and can be programmed to display a number that indicates the order. For example, the display can display a "1" to indicate a first scanner to be selected, a "2" to indicate a second scanner to be selected, a "3" to indicate a third scanner to be selected, etc.

The ultrasound system can be modular, in that the display device can be removably attached to the ultrasound cart. In a first configuration, the ultrasound system can operate when the display device is removed from the ultrasound cart. For instance, the ultrasound scanner and the display device can operate without assistance from the ultrasound cart to generate ultrasound images. In a second configuration, the ultrasound system can operate when the display device is attached to the ultrasound cart. The ultrasound cart can include a processor system, so that the ultrasound cart can provide enhanced functionality for operation in the second configuration compared to the first configuration. As an example, the processor system of the ultrasound cart can implement a neural network that can be too resource complex to be implemented on the ultrasound scanner or the display device. The neural network can thus provide enhanced functionality, e.g., by generating inferences and communicating the inferences to the display device for display. In one example, the inferences include classifications of blood vessels as veins or arteries.

As an example, an ultrasound system can include an ultrasound cart including a processor, an ultrasound scanner wirelessly coupled to a display device, and the display device implemented to be removably attached to the ultrasound cart. The processor, the display device, and the ultrasound scanner can be configured to implement a first ultrasound imaging mode when the display device is attached to the ultrasound cart. The display device and the ultrasound scanner can be configured to implement a second ultrasound imaging mode and not the first ultrasound imaging mode when the display device is removed from the ultrasound cart. The first ultrasound imaging mode can include B-mode imaging. The second ultrasound imaging mode can include M-mode imaging, Doppler imaging, super-resolution imaging, style-transfer imaging (e.g., images that are generated from a first image in the style of a second image), and the like.

At least one of the ultrasound cart and an ultrasound scanner can indicate that the ultrasound scanner requires cleaning. For example, the visual representation of the scanner holder displayed by the display device can indicate a cleanliness level of the scanners in the scanner holder. For instance, the cleanliness level can be indicated by a color of the visual representation, and/or an icon displayed as part of the visual representation. The ultrasound system can make the determination that scanner cleaning is required in any suitable way. In an example, the ultrasound system makes this determination based on the ultrasound scanner being removed and then returned to the scanner holder. The determination can be based on usage counts (e.g., used one or more times, etc.). In some embodiments, a camera can take an image of the scanner head and the system can make the determination based on an analysis of the image of the scanner head (e.g., detects the head has material on it, etc.).

A scanner can indicate that it needs to be cleaned in any suitable way. For instance, a display screen of the scanner can be programmed to display "cleaning required", an LED can be activated to indicate that cleaning is required, etc. In one example, the scanner is coated (e.g., wholly or partially, such as substantially all of the scanner surface except a lens through which ultrasound is transmitted and received). The coating can be a reactive coating that changes a visual property of the coating based on a property of the coating or a signal applied to the coating. For example, the coating can change its color based on an electrical signal applied to the surface of the scanner, an amount of light that has been absorbed by the coating, etc. By changing the color of the surface of the scanner, one can more easily and quickly determine that the scanner needs to be cleaned, compared to a simple LED status change.

In an example, the ultrasound system determines that the scanner needs to be cleaned based on a property of the surface of the scanner, such as a surface capacitance and/or resistance measured at one or more locations, e.g., across two regions, on the surface of the scanner. The ultrasound cart can measure the surface property of a scanner when it is placed in the scanner holder and again when it is returned to the scanner holder. If the difference in the surface property is above a threshold difference, such as one microfarad or one milliohm, then the ultrasound scanner, ultrasound cart, and/or display device can indicate that cleaning is required for the ultrasound scanner.

In an embodiment, the ultrasound cart includes an ultraviolet light source configured to emit ultraviolet light at the ultrasound scanners, in order to maintain a cleanliness level of the scanners. The scanner holder can include a lid over the scanners, and the lid can be used to both maintain cleanliness and act as a theft deterrent, which is especially important for wireless scanners. Additionally or alternatively, the ultrasound cart can include a mechanism for cleaning or disinfecting any of the accessories stored on the ultrasound cart, such as needle guides, electrocardiogram (ECG) modules, leakage testers, barcode scanners, medical grade printers, and other similar accessories. For instance, the ultrasound cart can include a pod in which scanners or other accessories can be cleaned. The pod can be filled with a gas, ultraviolet light, liquid, or any other suitable cleaning agent to disinfect an accessory. In an example, the pod covers wireless scanners while they are charging. Additionally or alternatively, the pod can include a dunk tank filled with a liquid cleaning agent in which scanners or other accessories can be placed. The pod may not be intended to replace standard and required cleaning procedures. Rather, the pod reduces risk and builds confidence that the accessories remain clean, such as after a standard sterilization procedure, since the care facility can be libel for infections acquired at the care facility.

Figure 7:
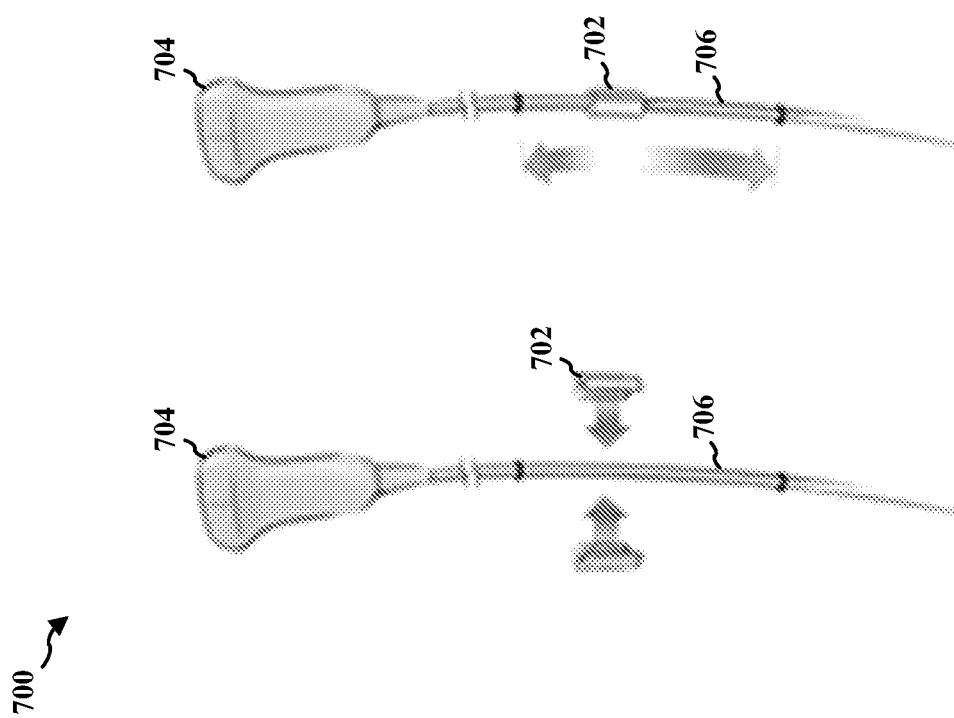
FIG. 7 is a diagram that illustrates a sleeve on a cable of a scanner for cable management.

FIG. 7 is a diagram 700 that illustrates a sleeve 702 on a cable 706 of a scanner 704 for cable management. The ultrasound system can include wired and/or wireless scanners. Accordingly, the ultrasound cart can include one or more mechanisms to manage the cables 706 of wired scanners 704. In one example, the cables 706 can include a metallic piece, such as a ferrite sleeve 702 that can be slid along the cable 706. The ultrasound cart can include a magnet, such as an electromagnet that can be activated and deactivated responsive to an electrical signal. In an example, the magnet is included as part of the scanner holder. The metallic piece on the cable 706 can be removably attached to the magnet on the ultrasound cart, e.g., based on the electrical signal that controls the electromagnet, to manage the cables 706 of the ultrasound scanners, keeping them secure and out of the way. An example of a ferrite sleeve 702 is illustrated in the diagram 700.

Figure 8:
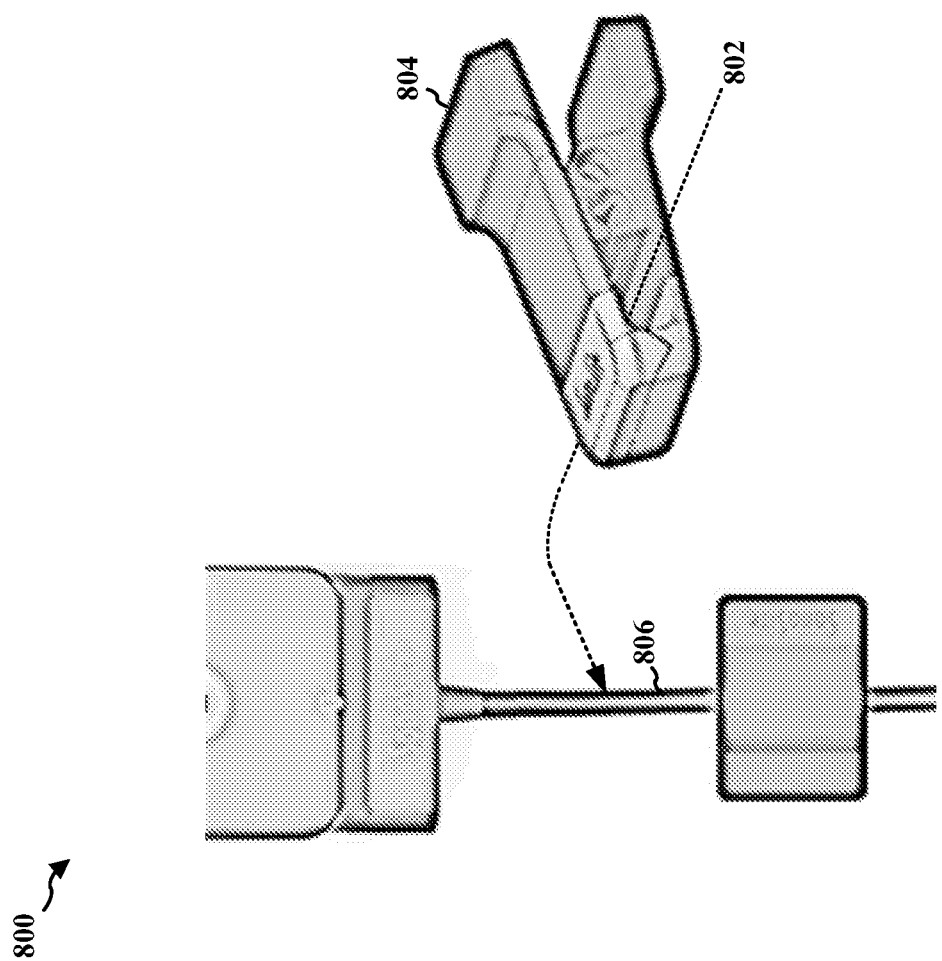
FIG. 8 is a diagram that illustrates a cable management clip.

FIG. 8 is a diagram 800 that illustrates a cable management clip 804. In one example, the cable management system of the ultrasound cart includes a clip 804 that attaches to the cable 806 of an ultrasound scanner, as illustrated in the diagram 800 based on 802. The clip 804 includes spring-loaded jaws. Slack of the cable 806 can be coiled up and placed in the spring-loaded jaws. The clip 804 can also be clamped, via the spring loaded jaws or an additional set of spring-loaded jaws, to the ultrasound cart, e.g., to the scanner holder.

The ultrasound system can include any suitable authentication and security system to make sure that authorized users are using the system, and to hinder theft (specifically of wireless scanners). In one example, the display device and/or ultrasound scanner can be disengaged, or unlocked, from the ultrasound cart by an authorized user, such as a registered ultrasound operator. For example, the authorized user can carry a key fob that unlocks the display device and/or ultrasound scanner for disengagement when the authorized user is within a prescribed distance from the ultrasound cart, such as ten feet. Additionally or alternatively, the display device and/or ultrasound scanner can include a handle or component that must be touched to unlock the display device and/or ultrasound scanner. The handle or component can include a capacitance sensor that senses the capacitance from the user touch. Additionally or alternatively, the ultrasound cart can include a reader for reading a badge or card carried by the authorized user, who can swipe the badge or card to unlock the display device and/or ultrasound scanner from the ultrasound cart. The ultrasound cart can include a voice recognition and identification system configured to recognize voice commands and identify the speaker of the command. The ultrasound cart can require that a certain command be spoken by a specified user to authenticate the user and allow a scanner to be removed from the scanner holder.

In an example, the ultrasound cart is configured to verify an authorized user without an active, dedicated authentication action by the user, and/or without knowledge by the user of the authentication, and/or without delay to the user caused by the authentication. For instance, the ultrasound cart can include a facial recognition algorithm, fingerprint reader on the handle of the ultrasound cart, ear region identifier, eye scanner, combinations thereof, and the like, to authenticate a user.

In one example, when a user is not authenticated, e.g., does not have a required badge or key fob, or fails a biometric authentication algorithm, the ultrasound system can implement an override mechanism to still allow the user to unlock and disengage the display device and/or ultrasound scanner so that it can be deployed at a point of care location, since a patient's care may critically depend on use of the ultrasound system. In this case, the system can require an additional step be performed by the user that would not be required if the user was properly authenticated, such as pressing a button on the ultrasound cart, e.g., a "release now" button. When this additional step is performed and the display device and/or ultrasound scanner is released, the ultrasound cart can generate an alert. The alert can be logged into a data file, emailed to a registered user for the ultrasound system (e.g., a last-known authorized user of the ultrasound system), emailed to an equipment administrator, displayed on a user interface of the display device, and the like. The alert can include text that describes the event, such as date, time, ultrasound system identification number, charge status of a scanner, and the like. Additionally or alternatively, the alert can include an image of the unauthenticated user to whom the ultrasound system is released. For instance, when the additional step is performed by the user to release the display device and/or ultrasound scanner from the utility cart, the ultrasound system can capture an image of the user with a camera integrated into the ultrasound cart, and/or with a security camera mounted in the care facility.

In an example, the wireless scanner includes a metallic portion, and the ultrasound cart includes an electromagnet that can be activated and deactivated responsive to an electrical signal in order to lock and unlock a wireless scanner to the scanner holder of the ultrasound cart, respectively. The scanner holder can include a mechanical lock (like a piston that engages a clasp) to lock a scanner to the scanner holder. In one example, the ultrasound system includes a proximity system that determines a distance of the ultrasound scanner to at least one of the display device and the ultrasound cart. If the proximity system determines that the distance is greater than a threshold distance, such as ten feet, the ultrasound scanner can automatically be disabled, and/or emit an audible alert, and/or emit a shock to the user to prevent theft.

In some embodiments, the ultrasound cart includes a motion mechanism, such as an electric motor and wheels, to facilitate autonomous movement. In one example, the ultrasound cart includes four wheels. In another example, the ultrasound cart includes one wheel in its base, and equilibrium is maintained automatically by gyroscopic sensors and computer-controlled motors. By using a single wheel in its based, the size of the footprint of the ultrasound cart can be reduced, compared to a multi-wheeled base. The ultrasound cart can include a failsafe mechanism to park the ultrasound cart and/or maintain equilibrium, e.g., in case a battery dies, or in the case of an emergency, such as an earthquake or fire.

An operator can instruct the ultrasound cart to move autonomously to a desired location in a care facility. The location can include a current location of the operator. To facilitate this autonomous movement, the ultrasound cart can include sensors, such as cameras, proximity sensors, etc., and have access to a map of the care facility. In one example, the ultrasound scanner sends a request to the ultrasound cart to move to a location of the ultrasound scanner when the battery level of the ultrasound scanner is below a threshold level, such as 15%, less than ten minutes operating time remaining based on the current battery level, etc. Multiple ultrasound carts can receive the request from the ultrasound scanner, and one of the ultrasound carts that has a redundant scanner to the scanner with the low battery can respond by going to the location of the low battery scanner. Hence, the system can automatically bring a redundant scanner to a sonographer when a first scanner has a low battery.

Figure 9:
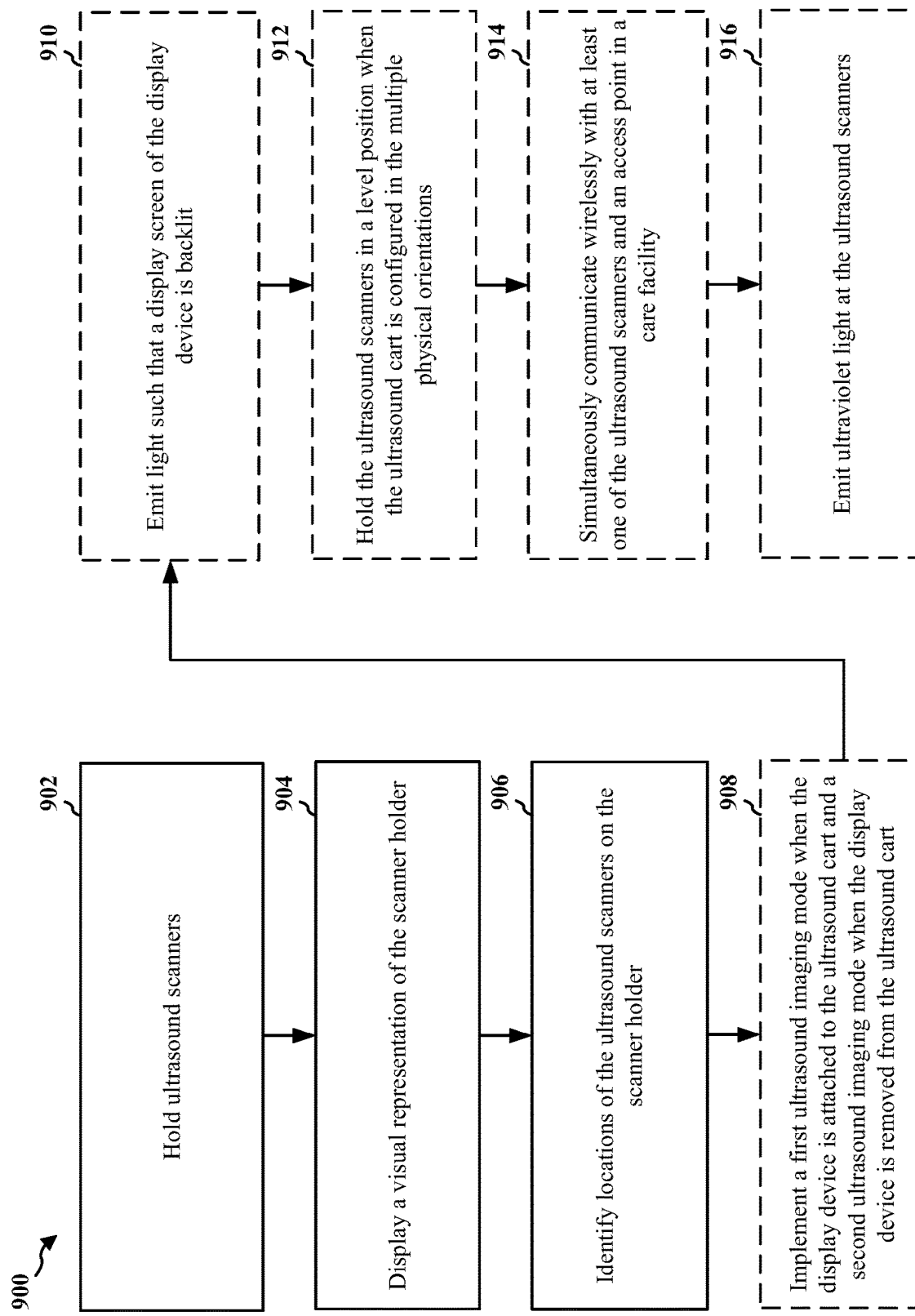
FIG. 9 is a data flow diagram of a process implemented by an ultrasound system.

FIG. 9 is a data flow diagram 900 of a process implemented by an ultrasound system. The process can be performed by processing logic that can include hardware (circuitry, dedicated logic, etc.), software (such as is run on a general-purpose computer system or a dedicated machine), firmware, or combinations thereof. In some embodiments, the ultrasound system includes an ultrasound cart having a scanner holder, a display device, and at least one ultrasound scanner. In some embodiments, the ultrasound system includes one or more processors and a memory coupled to the processor(s) to perform the process, and the one or more processors are coupled to the ultrasound cart having the scanner holder, the display device, and/or the at least one ultrasound scanner to perform the process of the data flow diagram 900.

The data flow diagram 900 illustrates example functions used by various embodiments. Although specific function blocks ("blocks") are disclosed in the data flow diagram 900, such blocks are examples. That is, embodiments are well suited to performing various other blocks or variations of the blocks recited in the data flow diagram 900. It is appreciated that the blocks in the data flow diagram 900 can be performed in an order different than presented, and that not all of the blocks in the data flow diagram 900 may be performed. At least a portion of the data flow diagram 900 can be performed based on aspects of FIGS. 1-8.

The data flow diagram 900 begins at block 902, where an ultrasound cart holds ultrasound scanners. For instance, the ultrasound cart can include a scanner holder to hold the ultrasound scanners. A scanner holder can include a battery charger implemented to charge a battery of the at least one of the ultrasound scanners. Further, the ultrasound cart can include a battery charger implemented to charge a battery of the display device.

At block 904, the display device displays a visual representation of the scanner holder. The display device can be implemented to receive a user input that selects an ultrasound scanner of the ultrasound scanners. The display device and the ultrasound scanner can also be implemented to pair with each other responsive to the user input. The visual representation can indicate the shape of the scanner holder and the locations for scanners in the scanner holder.

At block 906, the display device identifies locations of the ultrasound scanners on the scanner holder. For example, the visual representation can be implemented by the display device to indicate an order of the ultrasound scanners in an examination protocol. Additionally or alternatively, the visual representation can be implemented by the display device to indicate that the at least one of the ultrasound scanners is paired with the display device. Additionally or alternatively, the visual representation can be implemented by the display device to indicate a status of the ultrasound scanners, the status including at least one of a battery level, a cleaning state, or a scanner configuration.

At block 908, processing logic implements a first ultrasound imaging mode when the display device is attached to the ultrasound cart and implements a second ultrasound imaging mode when the display device is removed from the ultrasound cart. When the display device is removed from the ultrasound cart, the display device and the at least one of the ultrasound scanners may not be configured to implement the first ultrasound imaging mode.

At block 910, the ultrasound cart emits light such that a display screen of the display device is backlit. The display device can be implemented to be attached to the ultrasound cart, and the ultrasound cart can include a light source to emit the light for backlighting the display screen.

At block 912, the scanner holder of the ultrasound cart holds the ultrasound scanners in a level position. In examples, the ultrasound cart can be configured in multiple physical orientations, and the scanner holder holds the ultrasound scanners in a level position as the ultrasound cart is oriented at the multiple physical orientations.

At block 914, the ultrasound system simultaneously communicates wirelessly with at least one of the ultrasound scanners and an access point in a care facility. For example, the ultrasound cart can include a wireless hub configured to perform the simultaneous wireless communication.

At block 916, the ultrasound cart emits ultraviolet light at the ultrasound scanners. That is, the ultrasound cart can include an ultraviolet light source.

Figure 10:
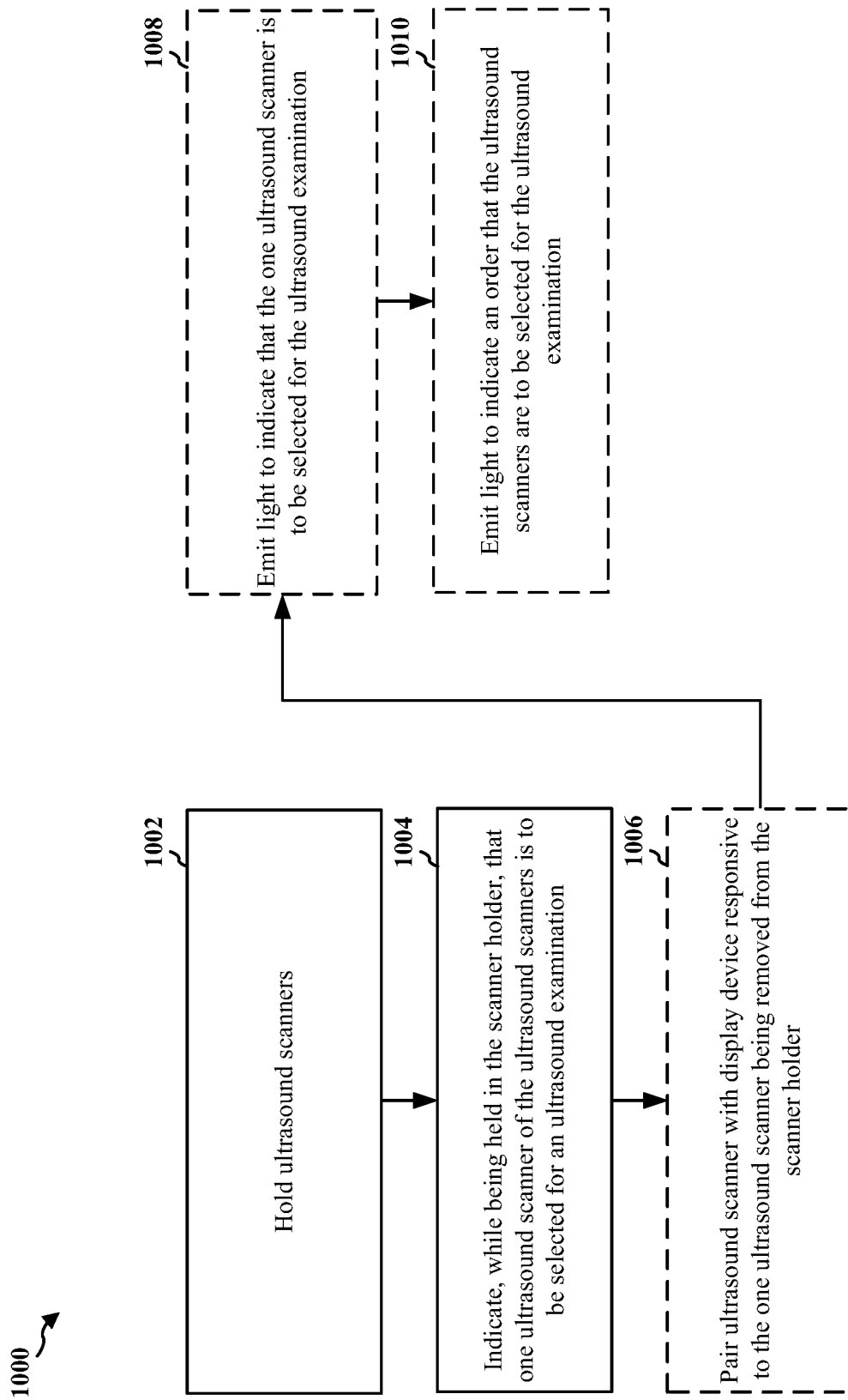
FIG. 10 is a data flow diagram of a process implemented by an ultrasound system.

FIG. 10 is a data flow diagram 1000 of a process implemented by an ultrasound system. The process can be performed by processing logic that can include hardware (circuitry, dedicated logic, etc.), software (such as is run on a general-purpose computer system or a dedicated machine), firmware, or combinations thereof. In some embodiments, the ultrasound system includes an ultrasound cart having a scanner holder, and ultrasound scanners. In some embodiments, the ultrasound system includes one or more processors and a memory coupled to the processor(s) to perform the process, and the one or more processors are coupled to the ultrasound cart having the scanner holder and/or the ultrasound scanners to perform the process of the data flow diagram 1000.

The data flow diagram 1000 illustrates example functions used by various embodiments. Although specific function blocks ("blocks") are disclosed in the data flow diagram 1000, such blocks are examples. That is, embodiments are well suited to performing various other blocks or variations of the blocks recited in the data flow diagram 1000. It is appreciated that the blocks in the data flow diagram 1000 can be performed in an order different than presented, and that not all of the blocks in the data flow diagram 1000 may be performed. At least a portion of the data flow diagram 1000 can be performed based on aspects of FIGS. 1-8.

The data flow diagram 1000 begins at block 1002, where an ultrasound cart holds ultrasound scanners. A scanner holder can include a battery charger implemented to charge a battery of the at least one of the ultrasound scanners. Further, the ultrasound cart can include a battery charger implemented to charge a battery of a display device.

At block 1004, the ultrasound scanners indicate, while being held in the scanner holder, that one ultrasound scanner of the ultrasound scanners is to be selected for an ultrasound examination. For example, the display device can be implemented to receive a user input that selects an ultrasound scanner of the ultrasound scanners.

At block 1006, the ultrasound system pairs the one ultrasound scanner with the display device responsive to the one ultrasound scanner being removed from the scanner holder. The display device and the one ultrasound scanner can be implemented to terminate said pair with each other responsive to the one ultrasound scanner being returned to the scanner holder. At least one of the ultrasound cart or the one ultrasound scanner is implemented to indicate, based on the one ultrasound scanner being returned to the scanner holder, that the one ultrasound scanner requires cleaning.

At block 1008, the one ultrasound scanner emits light to indicate that the one ultrasound scanner is to be selected for the ultrasound examination. For example, the one ultrasound scanner includes at least one light source.

At block 1010, the ultrasound scanners emit light to indicate an order that the ultrasound scanners are to be selected for the ultrasound examination. For example, the ultrasound scanners include light sources.

Figure 11:
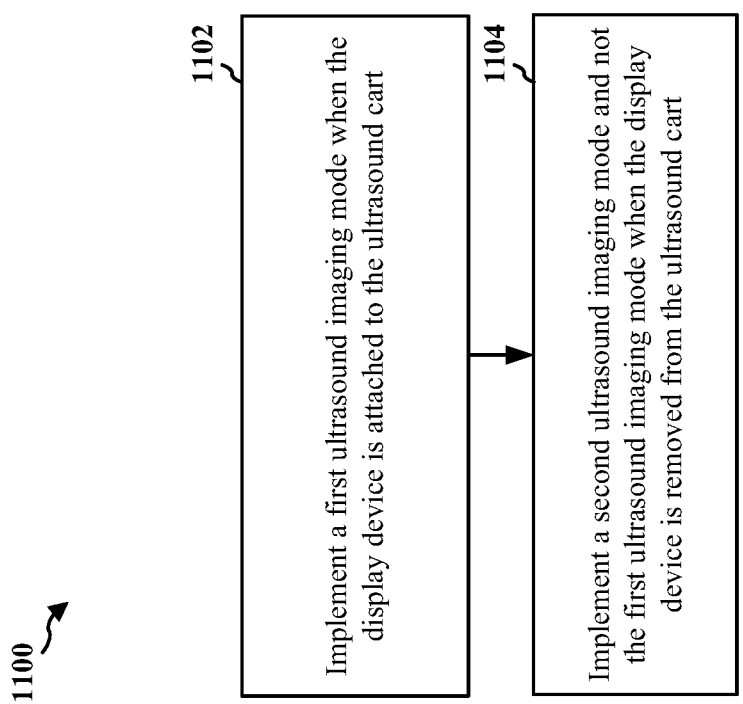
FIG. 11 is a data flow diagram of a process implemented by an ultrasound system.

FIG. 11 is a data flow diagram 1100 of a process implemented by an ultrasound system. The process can be performed by processing logic that can include hardware (circuitry, dedicated logic, etc.), software (such as is run on a general-purpose computer system or a dedicated machine), firmware, or combinations thereof. In some embodiments, the ultrasound system includes an ultrasound cart, a display device, and an ultrasound scanner wirelessly coupled to the display device. In some embodiments, the ultrasound system includes one or more processors and a memory coupled to the processor(s) to perform the process, and the one or more processors are coupled to the ultrasound cart, the display device, and/or the ultrasound scanner to perform the process of the data flow diagram 1100.

The data flow diagram 1100 illustrates example functions used by various embodiments. Although specific function blocks ("blocks") are disclosed in the data flow diagram 1100, such blocks are examples. That is, embodiments are well suited to performing various other blocks or variations of the blocks recited in the data flow diagram 1100. It is appreciated that the blocks in the data flow diagram 1100 can be performed in an order different than presented, and that not all of the blocks in the data flow diagram 1100 may be performed. At least a portion of the data flow diagram 1100 can be performed based on aspects of FIGS. 1-8.

The data flow diagram 1100 begins at block 1102, where processing logic implements a first ultrasound imaging mode when the display device is attached to the ultrasound cart. For example, the display device can be implemented to be removably attached to the ultrasound cart, the processor, and/or the display device. In examples, the ultrasound scanner implements the functionality of block 1102.

At block 1104, the processing logic implements a second ultrasound imaging mode and not the first ultrasound imaging mode when the display device is removed from the ultrasound cart. For example, the display device can be implemented to be removably attached to the ultrasound cart, the processor, and/or the display device. In examples, the ultrasound scanner implements the functionality of block 1104.

The specific order or hierarchy of blocks in the processes and flowcharts disclosed herein is an illustration of example approaches. Hence, the specific order or hierarchy of blocks in the processes and flowcharts can be rearranged. Some blocks can also be combined or deleted. Dashed lines may indicate optional elements of the diagrams that in some embodiments can be skipped. The accompanying method claims present elements of the various blocks in an example order, and are not limited to the specific order or hierarchy presented in the claims, processes, and flowcharts.

The detailed description set forth herein describes various configurations in connection with the drawings and does not represent the only configurations in which the concepts described herein may be practiced. The detailed description includes specific details for the purpose of providing a thorough explanation of various concepts. However, these concepts may be practiced without these specific details. In some instances, well known structures and components are shown in block diagram form in order to avoid obscuring such concepts.

The description herein is provided to enable a person skilled in the art to practice the various aspects described herein. Various modifications to these aspects will be readily apparent to those skilled in the art, and the generic principles defined herein may be applied to other aspects. Thus, the claims are not limited to the aspects described herein, but are to be interpreted in view of the full scope of the present disclosure consistent with the language of the claims.

Reference to an element in the singular does not mean "one and only one" unless specifically stated, but rather "one or more." Terms such as "if," "when," and "while" do not imply an immediate temporal relationship or reaction. That is, these phrases, e.g., "when," do not imply an immediate action in response to or during the occurrence of an action, but simply imply that if a condition is met then an action will occur, but without requiring a specific or immediate time constraint for the action to occur. Unless specifically stated otherwise, the term "some" refers to one or more. Combinations such as "at least one of A, B, or C" or "one or more of A, B, or C" include any combination of A, B, and/or C, such as A and B, A and C, B and C, or A and B and C, and may include multiples of A, multiples of B, and/or multiples of C, or may include A only, B only, or C only. Sets should be interpreted as a set of elements where the elements number one or more.

Unless otherwise specifically indicated, ordinal terms such as "first" and "second" do not necessarily imply an order in time, sequence, numerical value, etc., but are used to distinguish between different instances of a term or phrase that follows each ordinal term.

The following examples are illustrative only and can be combined with other examples or teachings described herein, without limitation.

Example 1 is an ultrasound system including: an ultrasound cart having a scanner holder configured to hold ultrasound scanners; a display device configured to display a visual representation of the scanner holder, the visual representation implemented to identify locations of the ultrasound scanners on the scanner holder; and at least one of the ultrasound scanners.

Example 2 can be combined with example 1 and includes that the visual representation is implemented to indicate an order of the ultrasound scanners in an examination protocol.

Example 3 can be combined with any of examples 1-2 and includes that the visual representation is implemented to indicate that the at least one of the ultrasound scanners is paired with the display device.

Example 4 can be combined with any of examples 1-3 and includes that the display device is implemented to receive a user input that selects an ultrasound scanner of the ultrasound scanners, and the display device and the ultrasound scanner are implemented to pair with each other responsive to the user input.

Example 5 can be combined with any of examples 1-4 and includes that the ultrasound cart includes a processor and the display device is implemented to be removably attached to the ultrasound cart, and includes that the processor is configured to implement a first ultrasound imaging mode when the display device is attached to the ultrasound cart, and includes that the display device and the at least one of the ultrasound scanners are configured to implement a second ultrasound imaging mode when the display device is removed from the ultrasound cart.

Example 6 can be combined with any of examples 1-5 and includes that when the display device is removed from the ultrasound cart, the display device and the at least one of the ultrasound scanners are not configured to implement the first ultrasound imaging mode.

Example 7 can be combined with any of examples 1-6 and includes that the scanner holder includes a battery charger implemented to charge a battery of the at least one of the ultrasound scanners.

Example 8 can be combined with any of examples 1-7 and includes that the ultrasound cart includes a battery charger implemented to charge a battery of the display device.

Example 9 can be combined with any of examples 1-8 and includes that the display device is implemented to be attached to the ultrasound cart, and the ultrasound cart includes a light source configured to emit light such that a display screen of the display device is backlit.

Example 10 can be combined with any of examples 1-9 and includes that the ultrasound cart can be configured in multiple physical orientations, and the scanner holder is configured to hold the ultrasound scanners in a level position when the ultrasound cart is configured in the multiple physical orientations.

Example 11 can be combined with any of examples 1-10 and includes that the ultrasound cart includes a wireless hub configured to simultaneously communicate wirelessly with the at least one of the ultrasound scanners and an access point in a care facility.

Example 12 can be combined with any of examples 1-11 and includes that the visual representation is implemented to indicate a status of the ultrasound scanners, the status including at least one of a battery level, a cleaning state, and a scanner configuration.

Example 13 can be combined with any of examples 1-12 and includes that the ultrasound cart includes an ultraviolet light source configured to emit ultraviolet light at the ultrasound scanners.

Example 14 is an ultrasound system including: an ultrasound cart having a scanner holder configured to hold ultrasound scanners; and the ultrasound scanners configured to indicate, while being held in the scanner holder, that one ultrasound scanner of the ultrasound scanners is to be selected for an ultrasound examination.

Example 15 can be combined with example 14 and further includes a display device, and includes that the one ultrasound scanner and the display device are implemented to pair with each other responsive to the one ultrasound scanner being removed from the scanner holder, and includes that the display device and the one ultrasound scanner are implemented to terminate said pair with each other responsive to the one ultrasound scanner being returned to the scanner holder.

Example 16 can be combined with any of examples 14-15 and includes that at least one of the ultrasound cart and the one ultrasound scanner is implemented to indicate, based on the one ultrasound scanner being returned to the scanner holder, that the one ultrasound scanner requires cleaning.

Example 17 can be combined with any of examples 14-16 and further includes a cable management device including a first portion implemented to attach to a cable of an ultrasound scanner of the ultrasound scanners and a second portion implemented to attach to the ultrasound cart.

Example 18 can be combined with any of examples 14-17 and includes that the one ultrasound scanner includes at least one light source configured to emit light to indicate that the one ultrasound scanner is to be selected for the ultrasound examination.

Example 19 can be combined with any of examples 14-18 and includes that the ultrasound scanners include light sources configured to emit light to indicate an order that the ultrasound scanners are to be selected for the ultrasound examination.

Example 20 is an ultrasound system including: an ultrasound cart including a processor; an ultrasound scanner wirelessly coupled to a display device; and the display device implemented to be removably attached to the ultrasound cart, the processor, the display device, and the ultrasound scanner being configured to implement a first ultrasound imaging mode when the display device is attached to the ultrasound cart, the display device and the ultrasound scanner being configured to implement a second ultrasound imaging mode and not the first ultrasound imaging mode when the display device is removed from the ultrasound cart.

Example 21 is a method for implementing the system as in any of examples 1-20.

Example 22 is at least one of an apparatus or a device that implements the system as in any of examples 1-20.

Example 23 is at least one of an apparatus or a device including means for implementing the system as in any of examples 1-20.

What is claimed is:

1. An ultrasound system comprising:
   an ultrasound cart having a scanner holder configured to hold ultrasound scanners; and
   the ultrasound scanners configured to indicate, while being held in the scanner holder, that one ultrasound scanner of the ultrasound scanners is to be selected for an ultrasound examination, wherein the ultrasound scanners include light sources configured to emit light to indicate an order that the ultrasound scanners are to be selected for the ultrasound examination;
   a display device, wherein the one ultrasound scanner and the display device are implemented to pair with each other responsive to the one ultrasound scanner being removed from the scanner holder, wherein the display device and the one ultrasound scanner are implemented to terminate said pair with each other responsive to the one ultrasound scanner being returned to the scanner holder, and
   wherein at least one of the ultrasound cart and the one ultrasound scanner is implemented to indicate, based on the one ultrasound scanner being returned to the scanner holder, that the one ultrasound scanner requires cleaning.

2. The ultrasound system as described in claim 1, wherein the one ultrasound scanner includes at least one light source configured to emit light to indicate that the one ultrasound scanner is to be selected for the ultrasound examination.

3. The ultrasound system as described in claim 1, wherein the display device is configured to display a visual representation of the scanner holder, the visual representation implemented to identify locations of the ultrasound scanners on the scanner holder.

4. The ultrasound system as described in claim 3, wherein the visual representation is implemented to indicate an order of the ultrasound scanners in an examination protocol.

5. The ultrasound system as described in claim 4, wherein the visual representation includes indicia arranged in a same shape as the scanner holder.

6. The ultrasound system as described in claim 5, wherein the indicia are not co-linear where scanner locations in the scanner holder are not co-linear.

7. The ultrasound system as described in claim 3, wherein the visual representation is implemented to indicate that the at least one of the ultrasound scanners is paired with the display device.

8. The ultrasound system as described in claim 3, wherein the display device is implemented to receive a user input that selects an ultrasound scanner of the ultrasound scanners, and the display device and the ultrasound scanner are implemented to pair with each other responsive to the user input.

9. The ultrasound system as described in claim 3, wherein the visual representation is implemented to indicate a status of the ultrasound scanners, the status including at least one of a cleaning state and a scanner configuration.

\* \* \* \* \*